(12) United States Patent
Doen et al.

(10) Patent No.: US 7,396,841 B2
(45) Date of Patent: Jul. 8, 2008

(54) INJECTIONS

(75) Inventors: Takayuki Doen, Suita (JP); Masao Nagao, Kashiba (JP); Naoki Asakawa, Takatsuki (JP); Nobuyuki Takechi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/344,805

(22) PCT Filed: Aug. 17, 2001

(86) PCT No.: PCT/JP01/07075

§ 371 (c)(1),
(2), (4) Date: Feb. 14, 2003

(87) PCT Pub. No.: WO02/15908

PCT Pub. Date: Feb. 28, 2002

(65) Prior Publication Data

US 2003/0191157 A1    Oct. 9, 2003

(30) Foreign Application Priority Data

Aug. 18, 2000 (JP) .............................. 2000-248468

(51) Int. Cl.
*A61K 31/4439* (2006.01)
*C07D 401/12* (2006.01)

(52) U.S. Cl. .................................. 514/338; 546/273.7

(58) Field of Classification Search ................ 514/338, 514/337; 546/273.7
See application file for complete search history.

(56) References Cited

U.S. PATENT DOCUMENTS

| 5,223,515 A | 6/1993 | Mikura et al. |
|---|---|---|
| 5,536,735 A | 7/1996 | Takechi et al. |
| 6,002,011 A | 12/1999 | Kato et al. ............... 546/273.7 |
| 2002/0039597 A1 | 4/2002 | Ukai et al. .................. 424/490 |

FOREIGN PATENT DOCUMENTS

| CA | 2 417 311 | 1/2003 |
|---|---|---|
| EP | 0356143 | 2/1990 |
| EP | 0382489 | 8/1990 |
| EP | 0649655 | 4/1995 |
| JP | 3-173817 | 7/1991 |
| JP | 6-92853 | 4/1994 |
| JP | 7-157440 | 6/1995 |
| JP | 08283158 | 10/1996 |
| JP | 11-507945 | 7/1999 |
| WO | WO 94/02141 | 2/1994 |
| WO | 97/17064 | 5/1997 |
| WO | WO 97/17064 | 5/1997 |
| WO | WO 99/00380 | 1/1999 |

*Primary Examiner*—Charanjit S Aulakh
(74) *Attorney, Agent, or Firm*—Hamre, Schumann, Mueller & Larson, P.C.

(57) ABSTRACT

An injectable composition comprises a benzimidazole compound having an antiulcer action and a strong alkali (e.g., an alkali metal hydroxide such as sodium hydroxide) in a proportion of about 1 equivalent of the latter relative to 1 mol of the former, and is substantially free from a nonaqueous solvent. The injectable composition may comprise N-methylglucamine, and a saccharide (such as mannitol). The injectable composition may be a freeze-dried preparation. The freeze-dried preparation is dissolvable in or dilutive with a distilled water for injection or an infusion solution without a nonaqueous solvent. The injectable composition is useful as an antiulcer agent.

29 Claims, 1 Drawing Sheet

INJECTIONS

This application is the National Phase filing of International Patent Application No. PCT/JP01/07075, filed Aug. 17, 2001.

TECHNICAL FIELD

The present invention relates to an injectable composition comprising a benzimidazole compound having an antiulcer action, and a process for producing the same.

BACKGROUND ART

As injectable compositions comprising a 2-[(2-pyridyl)methylsulfinyl]benzimidazole compound having an antiulcer action, for example, the following injectable compositions have been reported.

1) Japanese Patent Application Laid-Open No. 138213/1990 (JP-2-138213A) (EP 0356143) discloses an injectable solution which comprises a benzimidazole compound having an antiulcer action and at least one of ethanol, propylene glycol and polyethylene glycol. The literature also discloses an injectable solution which contains a freeze-dried product of the benzimidazole compound dissolved in a mixture solution of an acidic substance and a polyethylene glycol, and further contains a saccharide such as mannitol and N-methylglucamine. Further, in Example 4 of the literature, 1 g of lansoprazole was dispersed in a distilled water for injection, and 3 ml of 1N-aqueous sodium hydroxide solution was added thereto to dissolve lansoprazole, followed by addition of water to make up to the total of 50 ml. The mixture was subjected to sterile filtration. The resulting filtrate was filled in a portion into vials, followed by lyophilization. The lyophilized powder was dissolved in a dissolving solvent composed of N-methylglucamine, hydrochloric acid and a polyethylene glycol.

However, in the injectable solution, the specific liquid composition for dissolution containing an alcohol selected from ethanol, propylene glycol and a polyethylene glycol is required, and an excess of alkali (sodium hydroxide) is employed.

2) Japanese Patent Application Laid-Open No. 92853/1994 (JP-6-92853A) (WO94/02141) discloses an injection comprising a 2-[(2-pyridyl)methylsulfinyl]benzimidazole compound having an antiulcer activity or a salt thereof and an aqueous solvent without nonaqueous solvent, wherein the pH of the injection is not less than 9.5 and not more than 11.5. In Example of the literature, 1N sodium hydroxide (2.3 ml) is added to 21.3 g of sodium salt of omeprazole (20 g as omeprazole), and a water for injection is added thereto to adjust the pH to 11.5. After filtration for sterilization, this alkaline aqueous solution is charged in vials and is lyophilized, followed by dissolution of the lyophilized product in a physiological saline to give an omeprazole injection.

However, an excess of an alkali (sodium hydroxide) is employed in the injection with the use of an aqueous solvent containing no nonaqueous solvent. Thus, in order to prepare an injection solution with the use of a freeze-dried injection, such complicated operations are required as kneading a 2-[(2-pyridyl)methylsulfinyl]benzimidazole compound for wetting and then dissolving the compound. The kneading operation might cause the formation of an exogenous material due to contact of the using instruments with each other. Moreover, owing to the complicated operations, it takes many hours to dissolve, as a result, the high concentration of an alkali aqueous solution is contacted with carbon dioxide in an air to decrease pH of the solution so that the quality of the injection is sometimes deteriorated. Further, there is a possibility that an excess of an alkali causes a pain or dolor and a local irritation by an injection. Therefore, there has been a growing demand for such an injectable composition that there is no need to attach the exclusive dissolving solution for the injectable composition, that the amount of an alkali to be used is as small as possible, and that the kneading operation and the complicated dissolving operation are not required. Moreover, such injectable compositions are considerably needed as preventing pH of the injectable composition from decreasing upon producing and redissolving of the injectable composition, and as maintaining the quality of the injectable composition.

It is, therefore, an object of the present invention to provide an injectable composition having no need to attach the exclusive dissolving solution for the injectable composition and capable of being dissolved in or diluted with a physiological saline or an infusion solution, and a production process of the same.

Another object of the present invention is to provide an injectable composition dissolvable by a simple operation, and a production process of the same.

Still another object of the present invention is to provide such an excellent injectable composition that pH of the injectable composition does not decline and that a pain (or dolor) or a local irritation is relieved by decreasing the alkali amount to be used, and a production process of the same.

DISCLOSURE OF INVENTION

The inventors of the present invention did intensive research, and finally found that such an injectable composition that there is no need to attach the exclusive dissolving solution for the injectable composition and that the kneading operation and the complicated dissolving operation are not required can be obtained by using a 2-[(2-pyridyl)methylsulfinyl]benzimidazole compound having an antiulcer action and a strong alkali in molar ratio of about 1:1. The present invention was accomplished based on the above findings.

That is, the present invention relates to an injectable composition comprising a compound represented by the formula (I) or a salt thereof (hereinafter, sometimes referred to simply as the compound (I)):

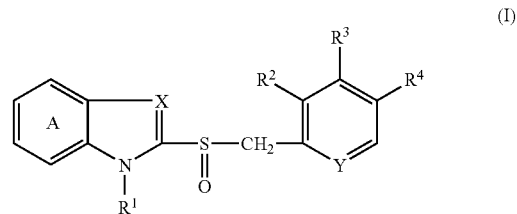

wherein a ring A represents a benzene ring which may have a substituent, $R^1$ represents a hydrogen atom, an aralkyl group which may have a substituent, an acyl group or an acyloxy group, $R^2$, $R^3$ and $R^4$ are same or different, each representing a hydrogen atom, an alkyl group which may have a substituent, an alkoxy group which may have a substituent, or an amino group which may have a substituent, X represents a nitrogen atom or CH, and Y represents a nitrogen atom or CH and a strong alkali in a proportion (ratio) of about 1 equivalent of the latter relative to 1 mol of the former.

In the formula (I), the ring A may represent a benzene ring which may have substituent(s) selected from the group consisting of a halogen atom, a $C_{1-4}$alkyl group which may be halogenated, a $C_{1-4}$alkoxy group which may be halogenated and a 5- or 6-membered heterocyclic group; $R^1$ may represent a hydrogen atom; $R^2$ may represent a $C_{1-6}$alkyl group, a $C_{1-6}$alkoxy group, a $C_{1-6}$alkoxy-$C_{1-6}$alkoxy group or a di-$C_{1-6}$alkylamino group, in particular a $C_{1-3}$alkyl group; $R^3$ may represent a hydrogen atom, a $C_{1-6}$alkoxy-$C_{1-6}$alkoxy group, or a $C_{1-6}$alkoxy group which may be halogenated, in particular a $C_{1-3}$alkoxy group which may be halogenated; $R^4$ may represent a hydrogen atom or a $C_{1-6}$alkyl group (e.g., a $C_{1-3}$alkyl group), in particular a hydrogen atom; and X and Y each may represent a nitrogen atom.

Further, the compound represented by the formula (I) may be a compound represented by the following formula (Ia):

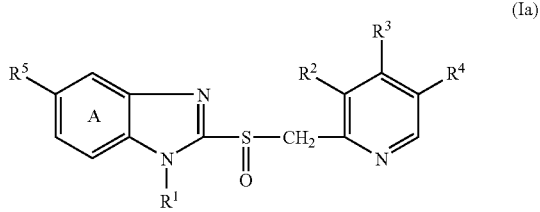

wherein $R^1$ represents a hydrogen atom; $R^2$ represents a $C_{1-3}$alkyl group or a $C_{1-3}$alkoxy group; $R^3$ represents a $C_{1-3}$alkoxy group which may be halogenated or may be substituted with a $C_{1-3}$alkoxy group; $R^4$ represents a hydrogen atom or a $C_{1-3}$alkyl group; and $R^5$ represents a hydrogen atom, a $C_{1-3}$alkoxy group which may be halogenated, or a pyrrolyl group.

In the formula (Ia), $R^1$ may represent a hydrogen atom; $R^2$ may represent a $C_{1-3}$alkyl group; $R^3$ may represent a $C_{1-3}$alkoxy group which may be halogenated; $R^4$ may represent a hydrogen atom; and $R^5$ may represent a hydrogen atom or a $C_{1-3}$alkoxy group which may be halogenated.

The injectable composition of the present invention is usually dissolvable in or dilutive with a solvent (a solvent of which a medium is substantially water) substantially free from a nonaqueous solvent (or a water-soluble organic solvent), and an injectable liquid composition can be easily prepared from the injectable composition.

The strong alkali may comprise an alkali metal compound (e.g., sodium hydroxide). The equivalent ratio of the strong alkali relative to 1 mol of the compound (I) may be about 0.90 to 1.10.

Incidentally, the solution of the injectable composition of the present invention may have a pH of about 10.4 to 12.0 in the case where the injectable composition is dissolved with the use of a physiological saline, or a distilled water for injection in a proportion of 2.5 ml relative to 15 mg of the compound (I). An osmotic pressure ratio of a dissolved solution, obtained by dissolving 15 mg of the compound (I) in 2.5 ml of a physiological saline, relative to the physiological saline may be about 0.3 to 5.

The injectable composition of the present invention may be a freeze-dried preparation, and such a freeze-dried preparation is dissolvable in or dilutive with a solvent substantially free from a nonaqueous solvent.

The injectable composition of the present invention may further comprise N-methylglucamine. The amount of N-methylglucamine may be about 0.1 to 1 mg relative to 1 mg of the compound (I). The injectable composition may further comprise a saccharide (e.g., a sugar alcohol such as mannitol). The amount of the saccharide may be about 0.1 to 20 mg relative to 1 mg of the compound (I). For example, an injectable composition containing such a component is an injectable composition comprising the compound (I), and being dissolvable in or dilutive with a solvent substantially free from a nonaqueous solvent, and may further comprise about 0.1 to 0.8 mg of N-methylglucamine and about 1 to 10 mg of a sugar alcohol relative to 1 mg of the compound (I).

Further, the injectable composition may, for example, be an injectable composition comprising the compound (I) and being dissolvable in or dilutive with a solvent substantially free from a nonaqueous solvent, and further comprising about 4 to 6 mg of N-methylglucamine, about 25 to 35 mg of mannitol and about 1.5 to 1.8 mg of a sodium hydroxide relative to 15 mg of the compound (I), e.g., an injectable composition comprising 30 mg of the compound (I), 3.45 mg of a sodium hydroxide, 10 mg of N-methylglucamine and 60 mg of mannitol, an injectable composition comprising 15 mg of the compound (I), 1.73 mg of a sodium hydroxide, 5 mg of N-methylglucamine and 30 mg of mannitol, and others.

The injectable composition of the present invention is usually dissolvable in or dilutive with a solvent of which a medium is substantially water, substantially free from a non-aqueous solvent (or a water-soluble organic solvent). Further, the injectable composition of the present invention may be a freeze-dried preparation (a freeze-dried injectable composition), for example, a freeze-dried preparation comprising the compound (I) and an alkali metal hydroxide in a molar ratio of 1:0.90 to 1.10, and further comprising about 0.1 to 0.8 mg of N-methylglucamine and about 1 to 10 mg of a sugar alcohol relative to 1 mg of the compound (I). Such a freeze-dried preparation is dissolvable in at least one liquid or solvent selected from waters for injection (a distilled water for injection), infusion solutions including an electrolyte liquid composition (such as a physiological saline), nutrition infusion solutions and others, and an injectable liquid composition can be easily prepared from the injectable composition.

The injectable composition of the present invention can be produced by dissolving the compound (I) in an aqueous solution of a strong alkali, wherein the concentration of the aqueous solution of the strong alkali is about 0.15 to 0.25 equivalent/L, and the amount of the aqueous solution of the strong alkali is about 1 equivalent relative to 1 mol of the compound (I). The present invention, therefore, includes an injectable composition obtained by the production process. In this process, the aqueous solution of the strong alkali may comprise an aqueous solution of sodium hydroxide.

Thus, in the present invention, the amount to be used of the strong alkali can be decreased, and the solubility of the compound (I) can be improved. The present invention, therefore, discloses a method for improving a relief of a pain or dolor and local irritation by an injectable composition, which comprises preparing the injectable composition with the use of the compound (I) and a strong alkali in a proportion of about 1 equivalent of the latter relative to 1 mol of the former without a nonaqueous solvent (or a water-soluble organic solvent); and a method for improving the solubility of the freeze-dried preparation in at least one liquid selected from waters for injection, infusion solutions and nutrition infusion solutions, without using a nonaqueous solvent (or a water-soluble organic solvent), which comprises preparing the freeze-dried preparation with the use of the compound (I) and a strong alkali in a proportion of about 1 equivalent of the latter relative to 1 mol of the former.

The present invention is useful as a method for preventing or treating digestive ulcer, gastritis, reflux esophagitis, NUD (Non-Ulcer Dyspepsia), gastric cancer, gastric MALT lymphoma, upper gastrointestinal hemorrhage, ulcer caused by a nonsteroidal anti-inflammatory agent, hyperacidity and ulcer due to postoperative stress, or disease due to *Helicobacter pylori*, which comprises administering the injectable composition to a human being.

Further, the present invention discloses use of an injectable composition comprising the compound represented by the formula (I) or a salt thereof and a strong alkali in a proportion of about 1 equivalent of the latter relative to 1 mol of the former for preventing or treating digestive ulcer, gastritis, reflux esophagitis, NUD (Non-Ulcer Dyspepsia), gastric cancer, gastric MALT lymphoma, upper gastrointestinal hemorrhage, ulcer caused by a nonsteroidal anti-inflammatory agent, hyperacidity and ulcer due to postoperative stress, or disease due to *Helicobacter pylori*. Moreover, the present invention also discloses use of a strong alkali for producing an injectable composition (for example, a freeze-dried preparation or a a freeze-dried injectable composition) comprising the compound (I) and the strong alkali in a proportion of about 1 equivalent of the latter relative to 1 mol of the former.

Incidentally, the term "an injectable composition" as used herein means not only a final injectable composition, but also an injectable composition precursor capable of preparing a final injectable composition with the use of a dissolving solvent upon using [for example, a liquid injectable composition (a concentrated or condensed injectable composition) or a solid injectable composition (such as a freeze-dried injectable composition)]. Moreover, in molar ratio of the compound (I) or a salt thereof and the strong alkali, the expression "about 1:1" means an equivalent ratio of the strong alkali relative to 1 mol of the compound (I) or the salt thereof. Further, the phrase "a salt of the compound represented by the formula (I)" means a salt to an acidic group and/or a basic group shown by the substituents, $R^1$ to $R^5$, in the formulae (I) and (Ia).

DETAILED DESCRIPTION OF THE INVENTION

Figure 1:
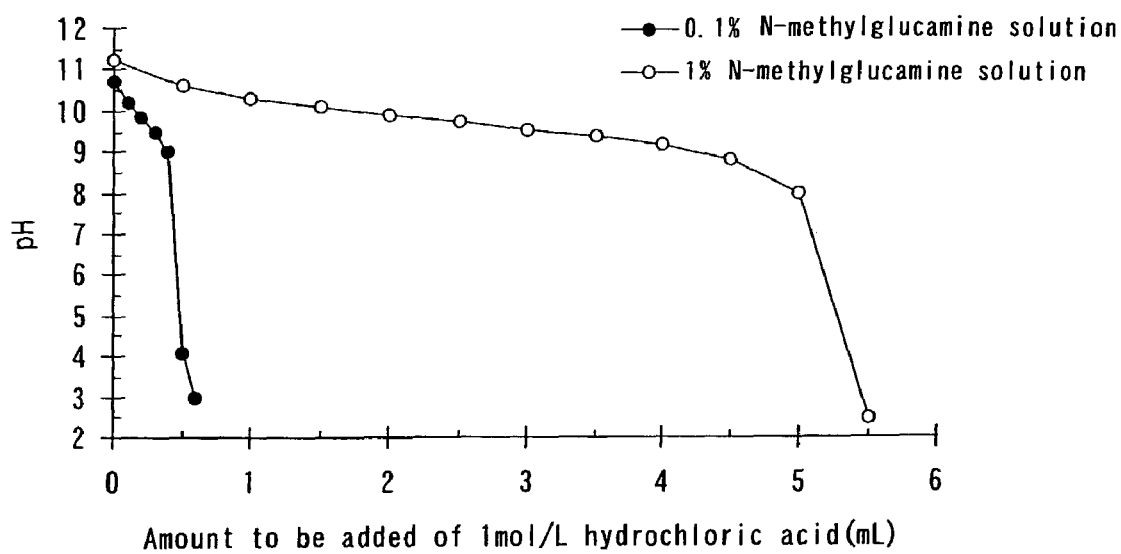
FIG. 1 is the graph demonstrating the results of Experimental Example 5.

The injectable composition of the present invention comprises the compound (I) and a strong alkali in equivalent ratio of about 1:1. That is, the injectable composition comprises about 1 equivalent of the strong alkali relative to 1 mol of the compound (I).

In the compound (I), examples of the "substituent" of the "benzene ring which may have a substituent" shown by the ring A include, for example, a halogen atom, a cyano group, a nitro group, an alkyl group which may have a substituent, a hydroxyl group, an alkoxy group which may have a substituent, an aryl group, an aryloxy group, a carboxyl group, an acyl group, an acyloxy group, and a 5- to 10-membered heterocyclic ring. The benzene ring may be substituted with about 1 to 3 substituents. When substituted with two or more substituents, each of substituents may be same or different. Among these substituents, a halogen atom, an alkyl group which may have a substituent, and an alkoxy group which may have a substituent are preferred.

As the halogen atom, there may be mentioned fluorine, chlorine, bromine atoms and the like. In Particular, a fluorine atom is preferred.

The "alkyl group" as the "alkyl group which may have a substituent" includes, for example, a $C_{1-7}$alkyl group (e.g., methyl, ethyl, propyl, isopropyl, butyl, isobutyl, sec-butyl, tert-butyl, pentyl, hexyl, and heptyl groups). The "substituent" as the "alkyl group which may have a substituent" includes, for example, a halogen atom, a hydroxyl group, a $C_{1-6}$alkoxy group (e.g., methoxy, ethoxy, propoxy, and butoxy groups), a $C_{1-6}$alkoxy-carbonyl group (e.g., methoxycarbonyl, ethoxycarbonyl, and propoxycarbonyl groups), and a carbamoyl group. The alkyl group may be substituted with about 1 to 3 substituents. When substituted with two or more substituents, each of substituents may be same or different.

The "alkoxy group" as the "alkoxy group which may have a substituent" includes, for example, a $C_{1-6}$alkoxy group (e.g., methoxy, ethoxy, propoxy, isopropoxy, butoxy, isobutoxy, and pentoxy groups). The "substituent" as the "alkoxy group which may have a substituent" includes the groups similar to those exemplified in the item of the "substituent" as the "alkyl group which may have a substituent", and the number to be substituted with the substituent is also same as that exemplified in the item of the "substituent" as the "alkyl group which may have a substituent".

As the "aryl group", there may be mentioned, for example, a $C_{6-14}$aryl group (e.g., phenyl, 1-naphthyl, 2-naphthyl, biphenyl, and 2-anthryl groups).

As the "aryloxy group", there may be mentioned, for example, a $C_{6-14}$aryloxy group (e.g., phenyloxy, 1-naphthyloxy, and 2-naphthyloxy groups).

Examples of the "acyl group" include formyl, alkylcarbonyl, alkoxycarbonyl, carbamoyl, alkylcarbamoyl, alkylsulfinyl, and alkylsulfonyl groups, etc.

The "alkylcarbonyl group" includes a $C_{1-6}$alkyl-carbonyl group (e.g., acetyl and propionyl groups).

The "alkoxycarbonyl group" includes a $C_{1-6}$alkoxy-carbonyl group (e.g., methoxycarbonyl, ethoxycarbonyl, propoxycarbonyl and butoxycarbonyl groups).

As examples of the "alkylcarbamoyl group", there may be mentioned an N-$C_{1-6}$alkyl-carbamoyl group (e.g., methylcarbamoyl and ethylcarbamoyl groups), an N,N-di$C_{1-6}$alkylcarbamoyl group (e.g., N,N-dimethylcarbamoyl, and N,N-diethylcarbamoyl groups).

Examples of the "alkylsulfinyl group" include, for example, a $C_{1-7}$alkylsulfinyl group (e.g., methylsulfinyl, ethylsulfinyl, propylsulfinyl, and isopropylsulfinyl groups).

Examples of the "alkylsulfonyl group" include, for example, a $C_{1-7}$alkylsulfonyl group (e.g., methylsulfonyl, ethylsulfonyl, propylsulfonyl, and isopropylsulfonyl groups).

The "acyloxy group" includes, for example, an alkylcarbonyloxy group, an alkoxycarbonyloxy group, a carbamoyloxy group, an alkylcarbamoyloxy group, an alkylsulfinyloxy group, and an alkylsulfonyloxy group.

As examples of the "alkylcarbonyloxy group", there may be mentioned a $C_{1-6}$alkyl-carbonyloxy group (e.g., acetyloxy and propionyloxy groups).

Examples of the "alkoxycarbonyloxy group" include, for example, a $C_{1-6}$alkoxy-carbonyloxy group (e.g., methoxycarbonyloxy, ethoxycarbonyloxy, propoxycarbonyloxy, and butoxycarbonyloxy groups).

The "alkylcarbamoyloxy group" includes a $C_{1-6}$alkyl-carbamoyloxy group (e.g., methylcarbamoyloxy and ethylcarbamoyloxy groups).

As examples of the "alkylsulfinyloxy group", there may be mentioned, for example, a $C_{1-7}$alkylsulfinyloxy group (e.g., methylsulfinyloxy, ethylsulfinyloxy, propylsulfinyloxy, and isopropylsulfinyloxy groups).

Examples of the "alkylsulfonyloxy group" include a $C_{1-7}$alkylsulfonyloxy group (e.g., methylsulfonyloxy, ethylsulfonyloxy, propylsulfonyloxy, and isopropylsulfonyloxy groups).

The "5- to 10-membered heterocyclic group" includes, for example, a 5- to 10-membered (preferably 5- or 6-membered) heterocyclic group having 1 or more (e.g., 1 to 3) hetero atoms selected from nitrogen atom, sulfur atom and oxygen atom other than carbon atom. The typical examples include 2- or 3-thienyl group, 2-, 3- or 4-pyridyl group, 2- or 3-furyl group, 1-, 2- or 3-pyrrolyl group, 2-, 3-, 4-, 5- or 8-quinolyl group, 1-, 3-, 4- or 5-isoquinolyl group, 1-, 2- or 3-indolyl group and the like. Among them, the preferred heterocyclic group includes a 5- or 6-membered heterocyclic group such as 1-, 2- or 3-pyrrolyl group.

It is preferred that the ring A is a benzene ring which may have 1 or 2 substituents selected from a halogen atom, a $C_{1-4}$alkyl group which may be halogenated, a $C_{1-4}$alkoxy group which may be halogenated, and a 5- or 6-membered heterocyclic group.

Preferred as a group represented by the following formula:

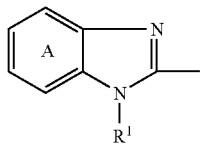

wherein each letter has the same meaning as mentioned above, is a group represented by the following formula:

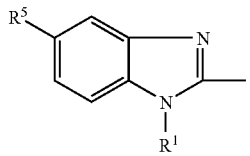

wherein $R^5$ represents a hydrogen atom, a $C_{1-4}$alkyl group which may be halogenated, an alkoxy group which may be halogenated, or a 5- or 6-membered heterocyclic group; $R^1$ has the same meaning as mentioned above.

$R^5$ is preferably (1) a hydrogen atom, (2) a $C_{1-3}$alkoxy group which may be halogenated, or (3) a pyrrolyl group (e.g., 1-, 2- or 3-pyrrolyl group). $R^5$ is usually a hydrogen atom, or a $C_{1-3}$alkoxy group which may be halogenated.

As the "aralkyl group" in the "aralkyl group which may have a substituent" shown by $R^1$, there may be mentioned, for example, a $C_{7-16}$aralkyl group (e.g., a $C_{6-10}$aryl-$C_{1-6}$alkyl group such as benzyl and phenethyl groups). As the "substituent" in the "aralkyl group which may have a substituent", there may be mentioned, for example, the groups similar to those exemplified in the item of the "substituent" as the "alkyl group which may have a substituent", and the number to be substituted with the substituent is about 1 to 4. When the number of the substituent is not less than 2, the substituents are same or different from each other.

The "acyl group" shown by $R^1$ includes, for example, the "acyl group" mentioned as the substituent of the ring A.

The "acyloxy group" shown by $R^1$ includes, for example, "the acyloxy group" mentioned as the substituent of the ring A.

The preferred $R^1$ is a hydrogen atom.

The "alkyl group which may have a substituent" shown by $R^2$, $R^3$ or $R^4$ includes the "alkyl group which may have a substituent" mentioned as the substituent of the ring A.

The "alkoxy group which may have a substituent" shown by $R^2$, $R^3$ or $R^4$ includes the "alkoxy group which may have a substituent" mentioned as the substituent of the ring A.

The "amino group which may have a substituent" shown by $R^2$, $R^3$ or $R^4$ includes, for example, an amino group, a mono-$C_{1-6}$alkylamino group (e.g., methylamino and ethylamino groups), a mono-$C_{6-14}$arylamino group (e.g., phenylamino, 1-naphthylamino, and 2-naphthylamino groups), a di-$C_{1-6}$alkylamino group (e.g., dimethylamino and diethylamino groups), a di-$C_{6-14}$arylamino group (e.g., diphenylamino group).

The preferred $R^2$ is a $C_{1-6}$alkyl group, a $C_{1-6}$alkoxy group, a $C_{1-6}$alkoxy-$C_{1-6}$alkoxy group, and a di-$C_{1-6}$alkylamino group. The further preferred R is a $C_{1-3}$alkyl group or a $C_{1-3}$alkoxy group.

The preferred $R^3$ is a hydrogen atom, a $C_{1-6}$alkoxy-$C_{1-6}$alkoxy group, or a $C_{1-6}$alkoxy group which may be halogenated. The further preferred R is a $C_{1-3}$alkoxy group which may be halogenated or may be substituted with a $C_{1-3}$alkoxy group.

The preferred $R^4$ is a hydrogen atom or a $C_{1-6}$alkyl group. The further preferred $R^4$ is a hydrogen atom or a $C_{1-3}$alkyl group (in particular, a hydrogen atom).

The preferred X is a nitrogen atom.

The preferred Y is a nitrogen atom.

The typical examples of the compound (I) includes the following compounds:

2-[[[3-methyl-4-(2,2,2-trifluoroethoxy)-2-pyridinyl]methyl]sulfinyl]-1H-benzimidazole, 2-[[(3,5-dimethyl-4-methoxy-2-pyridinyl)methyl]sulfinyl]-5-methoxy-1H-benzimidazole, a sodium salt of 2-[[[4-(3-methoxypropoxy)-3-methyl-2-pyridinyl]methyl]sulfinyl]-1H-benzimidazole, 5-difluoromethoxy-2-[[(3,4-dimethoxy-2-pyridinyl)methyl]sulfinyl]-1H-benzimidazole, and the like.

Among them, 2-[[[3-methyl-4-(2,2,2-trifluoroethoxy)-2-pyridinyl]methyl]sulfinyl]-1H-benzimidazole is preferred.

Incidentally, the compound (I) may be a racemic compound, and may be an optically active substance such as a R-isomer or a S-isomer. For example, the compound (I) may be an optically active substance such as (R)-2-[[[3-methyl-4-(2,2,2-trifluoroethoxy)-2-pyridinyl]methyl]sulfinyl]-1H-benzimidazole.

The salt of the compound represented by the formula (I) preferably includes a pharmaceutically acceptable salt, for example, a salt with an inorganic base, a salt with an organic base, a salt with a basic amino acid and the like.

As the preferred examples of the salt with an inorganic base, there may be mentioned, for example, an alkali metal salt such as a sodium salt and a potassium salt; an alkaline earth metal salt such as a calcium salt and a magnesium salt; and an ammonium salt.

The preferred examples of the salt with an organic base include, for example, a salt with an alkylamine (e.g., trimethylamine, triethylamine), a heterocyclic amine (e.g., pyridine, picoline), an alkanolamine (e.g., ethanolamine, diethanolamine, triethanolamine), dicyclohexylamine, N,N'-dibenzylethylenediamine or the like.

The preferred examples of the salt with a basic amino acid include, for example, a salt with arginine, lysine, ornithine or the like.

Among these salts, the alkali metal salt or the alkaline earth metal salt is preferred. In particular, the sodium salt is preferred.

The compound (I) can be prepared by per se known methods, for example, the methods described in Japanese Patent Application Laid-Open No. 50978/1986 (JP-61-50978A), U.S. Pat. No. 4,628,098, Japanese Patent Application Laid-Open No. 195068/1998 (JP-10-195068A), WO 98/21201 or methods based on these methods. Incidentally, an optically active compound (I) can be obtained by an optical resolution method (e.g., a fractional recrystallization method, a chiral column method, a diastereomer method, a method with a microorganism or an enzyme), an asymmetric oxidation method.

It is sufficient that the "strong alkali" has a strong basisity, and the "strong alkali" may be a base such as a hydroxide, or may be in the form of a salt such as carbonate and acetate. As the base, there may be mentioned a compound having a large degree of electrolytic dissociation in an aqueous solution, for example, a compound having a degree of electrolytic dissociation of not less than about 0.5. Moreover, although most of salts are strong electrolytes, a basic substance having pH of about not less than 11, particularly about not less than 11.5 in an aqueous solution is preferred. As such strong alkalis, there may be mentioned, for example, an alkali metal compound (e.g., an alkali metal hydroxide such as sodium hydroxide and potassium hydroxide, an alkaline earth metal carbonate such as sodium carbonate and potassium carbonate), a strong basic substance such as arginine. These strong alkalis can be used singly or in combination. The preferred strong alkali includes the alkali metal compound, for example, the alkali metal hydroxide (e.g., sodium hydroxide, potassium hydroxide) in particular, sodium hydroxide.

The content of the "strong alkali" is about 1 equivalent, preferably about 0.80 to 1.20 equivalents, more preferably about 0.90 to 1.10 (e.g., about 0.95 to 1.08) equivalents, and particularly about 0.97 to 1.08 (e.g., about 1.0 to 1.08) equivalents relative to 1 mol of the compound (I).

According to the present invention, the amount of the strong alkali can be decreased, and the solubility of the injectable composition can be improved with being substantially free from using a nonaqueous solvent (or a water-soluble organic solvent). Therefore, the present invention also discloses use of a strong alkali for producing the above injectable composition.

The injectable composition of the present invention may further comprise N-methylglucamine. The content of the "N-methylglucamine" is about 0.1 to 1 mg, preferably about 0.1 to 0.8 mg, more preferably about 0.2 to 0.6 mg and particularly about 0.3 to 0.5 mg (e.g., about 0.3 to 0.4 mg) relative to 1 mg of the compound (I).

Addition of N-methylglucamine enables to prevent pH from declining owing to buffer action of N-methylglucamine and enables to inhibit deterioration of the quality of a preparation due to precipitation of impurities. Further, by incorporating N-methylglucamine, such a high pH can be maintained as about 9 to 11, and further, as about 8 to 11 can be retained depending on the concentration.

The "injectable composition" of the present invention may further comprise a saccharide (a sugar). As the "saccharide", there may be mentioned, for example, a monosaccharide (e.g., glucose, galactose, ribose, xylose, mannose, maltotriose, maltotetraose), a disaccharide (e.g., sucrose, lactose, cellobiose, maltose), a trisaccharide (e.g., raffinose), a sugar alcohol (e.g., sorbitol, inositol, mannitol), a polysaccharide (e.g., dextran, chondoroitin sulfate, hyaluronic acid, dextrin sulfate) and a salt thereof (e.g., sodium salt of chondoroitin sulfate, sodium salt of hyaluronic acid), a cyclic saccharide (e.g., cyclodextrin, branched cyclodextrin). Of these saccharides, a sugar alcohol is preferred. Mannitol is particularly preferred.

The content of the "saccharide" is about 0.1 to 20 mg, preferably about 0.5 to 10 mg (e.g., about 1 to 10 mg), more preferably about 1 to 5 mg (e.g., about 1 to 3.3 mg) relative to 1 mg of the compound (I).

The injectable composition of the present invention may further comprise an additive.

As the "additive", there may be mentioned, for example, a water-soluble inorganic acid (e.g., hydrochloric acid, sulfuric acid, carbonic acid, phosphoric acid), an alkali metal salt of a water-soluble inorganic acid (e.g., sodium chloride, potassium chloride, sodium sulfate, potassium sulfate), an alkaline earth metal salt of a water-soluble inorganic acid (e.g., calcium chloride, magnesium chloride), a water-soluble organic acid (e.g., citric acid, tartaric acid, lactic acid, succinic acid, malic acid, acetic acid, oxalic acid, benzoic acid, tannic acid, gluconic acid, fumaric acid, sorbic acid, erysorbic acid, mesylic acid, mefenamic acid), an alkali metal salt of a water-soluble organic acid (e.g., sodium citrate, sodium tartarate), an alkaline earth metal salt of a water-soluble organic acid (e.g., calcium citrate, calcium lactate, magnesium gluconate), a neutral amino acid (e.g., glycine, alanine), an acidic amino acid (e.g., aspartic acid, glutamic acid), a salt of an acidic amino acid (e.g., sodium aspartate, potassium glutamate), a salt of a basic amino acid (e.g., lysine hydrochloride, arginine hydrochloride).

Moreover, if necessary, in the "injectable composition" of the present invention may be employed a buffer (e.g., sodium dihydrogenphosphate, disodium hydrogenphosphate), an isotonizing agent (e.g., glucose, sodium chloride), a stabilizer (e.g., sodium hydrogensulfite), a soothing agent (e.g., glucose, benzyl alcohol, mepivacaine hydrochloride, xylocaine hydrochloride, procaine hydrochloride, carbocaine hydrochloride), a preservative (e.g., p-oxybenzoate such as methyl p-oxybenzoate and propyl p-oxybenzoate, thymelosal, chlorobutanol, benzyl alcohol).

The typical examples of the injectable composition of the present invention include an injectable composition comprising the compound (I), a strong alkali (e.g., an alkali metal hydroxide), N-methylglucamine and a saccharide. The preferred injectable composition includes an injectable composition comprising the compound (I), sodium hydroxide, N-methylglucamine and mannitol. In such an injectable composition, the amount of each component may be about 4 to 6 mg of N-methylglucamine, about 25 to 35 mg of a sugar alcohol (e.g., mannitol) and about 1.5 to 1.8 mg of sodium hydroxide relative to 15 mg of the compound (I). More specifically, the injectable composition may be an injectable composition comprising 30 mg of the compound (I), 3.45 mg of sodium hydroxide, 10 mg of N-methylglucamine and 60 mg of mannitol (hereinafter, sometimes referred to simply as the preparation (I)), or an injectable composition comprising 15 mg of the compound (I), 1.73 mg of sodium hydroxide, 5 mg of N-methylglucamine and 30 mg of mannitol (hereinafter, sometimes referred to simply as the preparation (II)).

The injectable composition of the present invention may be in the form of a liquid (e.g., in the form of an aqueous injection solution), or may be in the form of a semi-solid (e.g., concentrated aqueous injectable composition) or a solid. The preferred injectable composition of the present invention is a freeze-dried preparation (freeze-dried injectable composition). The injectable composition of the present invention also includes an injectable composition dissolved in or diluted with a dissolving liquid composition or a diluting liquid composition upon using.

The injectable composition of the present invention (in particular, a freeze-dried preparation) can be dissolved in or diluted with an aqueous dissolving liquid composition or diluting liquid composition such as a dissolving liquid composition or a diluting liquid composition substantially free from a nonaqueous solvent (e.g., a water-soluble organic solvent such as propylene glycol and polyethylene glycol), for example, a water for injection such as a distilled water for injection, an infusion solution (e.g., an electrolyte liquid composition such as a physiological saline) so that the injectable composition can be easily prepared. Therefore, the injectable composition of the present invention is, usually, substantially free from a nonaqueous solvent (e.g., a water-soluble organic solvent such as propylene glycol and polyethylene glycol). Moreover, in an aqueous injectable composition (injection solution), the solubility of the compound (I) is not deteriorated even when a solvent is substantially water (e.g., a distilled water). Further, since the amount to be used of the strong alkali can be decreased without a nonaqueous solvent, a pain or dolor and a local irritation of the injectable composition can be relieved and decline of pH of the injectable composition can be inhibited. Therefore, the present invention also discloses a method for improving a relief of a pain or dolor and local irritation by an injectable composition and a method for improving a solubility of the injectable composition (especially, a freeze-dried preparation).

The injectable composition of the present invention has a pH of about 10.4 to 12.0, preferably about 10.5 to 11.5 and more preferably about 10.6 to 11.3 in the case where 15 mg of the compound (I) is dissolved in 2.5 ml of a physiological saline, or a distilled water for injection. In other words, in a solution obtained by redissolving the preparation (I) in 5 ml of a physiological saline or a water for injection and a solution obtained by redissolving the preparation (II) in 2.5 ml of a physiological saline or a water for injection, each solution usually has the above pH. When the preparation (I) is further diluted with up to about 1 L of a physiological saline, pH of the preparation (I) is about 9 to 11.

Incidentally, an aqueous solution of N-methylglucamine has a sufficient buffer activity at pH of about 9 to 11 so that the decline of pH of a solution containing the compound (I) can be inhibited and the deterioration of the quality can be suppressed upon producing an injectable composition comprising the compound (I) and redissolving the injectable composition.

Further, in the case where 15 mg of the compound (I) is dissolved in 2.5 ml of a physiological saline, an osmotic pressure ratio of the resultant dissolved solution relative to the physiological saline is, for example, about 0.3 to 5, preferably about 0.5 to 3, and more preferably about 1 to 2. In other words, in a solution obtained by dissolving the preparation (I) in 5 mL of a physiological saline and a solution obtained by dissolving the preparation (II) in 2.5 mL of a physiological saline, each solution usually has the above osmotic pressure ratio (when an osmotic pressure of 0.9% physiological saline is assumed to be 1).

The injectable composition of the present invention can be produced by dissolving the compound (I) in a strong alkali aqueous solution (e.g., an aqueous solution of sodium hydroxide) and filling the solution into a vial or an ampoule, and if necessary, lyophilizing the solution. When N-methylglucamine, a saccharide and an additive are added, an injectable composition can be obtained by dissolving the compound (I), N-methylglucamine, a saccharide and an additive etc. in a strong alkali aqueous solution (e.g., an aqueous solution of sodium hydroxide) and filling the solution into a vial or an ampoule, and if necessary, lyophilizing the solution. In particular, an injectable composition can be produced by dissolving the compound (I) into a strong alkali aqueous solution having a specific concentration (e.g., an aqueous solution of sodium hydroxide) in a proportion of about 1 equivalent of the strong alkali (e.g., sodium hydroxide) relative to 1 mol of the compound (I).

The concentration of the "strong alkali aqueous solution" is about 0.15 to 0.25 equivalent/L, preferably about 0.17 to 0.23 equivalent/L and in particular about 0.18 to 0.22 equivalent/L (e.g., about 0.19 to 0.21 mol/L). In other words, for example, in the case where sodium hydroxide is employed as the strong alkali, the concentration of the "sodium hydroxide aqueous solution" is about 0.15 to 0.25 mol/L, and preferably about 0.18 to 0.22 mol/L. In the case where the concentration of the sodium hydroxide is less than 0.1 mol/L, the enough solubility cannot be obtained and the compound (I) cannot be dissolved completely so that the resultant dissolved solution becomes white-turbid. In the case where the concentration is more than 0.25 mol/L, the sufficient kneading operation followed by diluting with a water for injection are required for dissolving the compound (I) so that very complicated operations are needed. Incidentally, in the case where a strong alkali other than sodium hydroxide is employed as the strong alkali, the injectable composition of the present invention can be also produced according to the above method.

The "dissolving" of the compound (I) in a strong alkali aqueous solution may be carried out by per se known methods.

The "freeze-drying (lyophilization)" may be carried out by per se known methods, and is desirably conducted by freezing a solution at a temperature of not higher than −25° C., and drying the resultant with elevating the shelf temperature to 25 to 40° C. while retaining a vacuum degree of a drying oven at a pressure of not more than about 13.3 Pa, in general.

As the "vial", one made of a glass capable of employing for an injectable composition is preferred. The preferred "vial" is USP TYPE I, II, III or the like, particularly TYPE I. Moreover, such a glass vial that decreases the amount to be eluted of an alkali more than usual, or a plastic vial such as a vial made from a cyclic polyolefin [e.g., CZ vial manufactured by Daikyo Seiko, Ltd.] is also employed. The configuration and the size of the vial are not particularly limited. The capacity of the vial is preferably not more than 100 mL, more preferably not more than 40 mL, and particularly not more than 20 mL. The typical examples of vials include, for example, 17P vial, 9P vial, 5P vial, and 3.5P vial.

As the "ampoule", one made of a glass capable of employing for an injectable composition is preferred. The configuration and the size of the ampoule are not particularly limited. The capacity of the ampoule is preferably not more than 30 mL, more preferably not more than 20 mL, and particularly not more than 10 mL. The typical examples of ampoule include, for example, 10P ampoule, 5P ampoule, and 3P ampoule.

Upon redissolving the injectable composition of the present invention, in the case where it takes many hours to become transparent due to vigorous foaming of the contents, the redissolving time can be reduced by using a vial or an ampoule coated with a silicone. As the silicone to be used in coating, there may be mentioned, a silicone oil such as a poly(dimethylsiloxane), a poly(methylhydrogensiloxane); a varnish silicone such as a methyl varnish silicone and a methyl phenyl varnish silicone. As one example of the preferred silicone, there may be mentioned KM-740 [manufactured by Shin-Etsu Chemical Co., Ltd.].

In the case where the injectable composition of the present invention is an aqueous injectable composition, a predetermined amount of the injectable composition is pulled out by means of an injection syringe from a vial or an ampoule to be used. In the case where the injectable composition of the present invention is a freeze-dried preparation, the preparation is utilized with redissolving upon using.

As to the "solvent for redissolving", there is no need to employ a solution containing such a nonaqueous solvent as might exhibit a toxicity when used in high concentration (e.g., polyethylene glycol). Examples of the solvent for redissolving include, for example, a water for injection (a distilled water for injection), an infusion solution [an electrolyte liquid composition (e.g., a physiological saline, a Ringer's solution), a nutrition infusion solution (a carbohydrate solution (e.g., a glucose solution such as 5% (w/v) glucose solution), an injectable liquid composition of a protein amino acid, an injectable liquid composition of a vitamin), a blood substitute combined an electrolyte liquid composition or a nutrition infusion solution (e.g., a carbohydrate solution), a fat emulsion preparation emulsifying fat], and a mixed solvent of two kinds or more thereof. To the solvent may be optionally added a pH-adjusting agent (e.g., an acidic substance, a weak-alkaline substance). Incidentally, the injectable composition of the present invention may be redissolved in an organic solvent such as ethanol, propylene glycol and polyethylene glycol, and after dissolving in the organic solvent, the injectable composition may be further diluted with the above "solvent for redissolving" to be used.

The "electrolyte liquid composition" is a liquid composition obtained by dissolving an electrolyte in a water for injection, and includes, for example, a solution comprising one or more kinds of sodium chloride, potassium chloride, calcium chloride, sodium lactate, sodium dihydrogenphosphate, magnesium carbonate and the like, a Ringer's solution of lactic acid, a Ringer's solution of acetic acid. The preferred electrolyte liquid composition includes a solution containing sodium chloride, in particular, a physiological saline [0.9% (w/v) sodium chloride solution].

The "carbohydrate solution (liquid composition)" is a liquid composition obtained by dissolving a saccharide in a water for injection, and includes, for example, a solution containing one or more kinds of glucose, fructose, sorbitol, mannitol, dextran and the like. The preferred saccharide solution includes 5 to 70% (w/v) glucose solution, especially, 5% (w/v) glucose solution and 10% (w/v) glucose solution.

The "injectable liquid composition of a protein amino acid" is a liquid composition obtained by dissolving an amino acid in a water for injection, and includes, for example, a solution containing one or more kinds of glycine, aspartic acid, lysine and the like.

The "injectable liquid composition of a vitamin" is a liquid composition obtained by dissolving a vitamin in a water for injection, and includes, for example, a solution containing one or more kinds of vitamin B1, vitamin C and the like.

The preferred "a solvent for redissolving" includes a water for injection, a physiological saline, and a glucose solution (e.g., 5% (w/v) glucose solution).

According to the injectable composition of the present invention, the solubility of the compound (I) does not decline, and there is no need to employ such a nonaqueous solvent as has a possibility of toxicity when used in high concentration (e.g., polyethylene glycol). Therefore, there is no need to attach a dissolving solution containing a nonaqueous solvent to the injectable composition, and the injectable composition is capable of being dissolved in or diluted with various infusion solutions upon being used at a hospital. Moreover, the injectable composition of the present invention has an excellent stability.

Further, according to a production process of the injectable composition of the present invention, the injectable composition can be produced with a minimum amount of sodium hydroxide to be required, and such an injectable composition that a pain or dolor and a local irritation are relieved can be obtained. Furthermore, since a freeze-dried preparation is simply produced, pH does not decrease due to contact with carbon dioxide in an air, and the high quality injectable composition can be obtained. Moreover, when N-methylglucamine is added, the decline of pH upon producing the injectable composition or after redissolving the injectable composition can be inhibited, and the higher quality injectable composition prevented from deteriorating a quality thereof can be provided.

The compound (I) has an excellent antiulcer action, gastric acid secretion-inhibiting action, mucosa-protecting action, anti-Helicobacter pylori action, etc., and has low toxicity.

The injectable composition of the present invention is useful in mammals (e.g., human beings, non-humans such as monkeys, sheep, bovines, horses, dogs, cats, rabbits, rats, mice, etc.) for the treatment and prevention of digestive (peptic) ulcer (e.g., gastric ulcer, duodenal ulcer, stomal ulcer, Zollinger-Ellison syndrome, etc.), gastritis, reflux esophagitis, NUD (Non-Ulcer Dyspepsia), gastric cancer (inclusive of gastric ulcer accompanied with enhanced production of interleukin-1β due to genetic polymorphism of interleukin-1), gastric MALT lymphoma; disease due to Helicobacter pylori; upper gastrointestinal hemorrhage due to digestive ulcer (peptic ulcer), acute stress ulcer and hemorrhagic gastritis; upper gastrointestinal hemorrhage due to invasive stress (stress from major surgery necessitating intensive management after surgery, and from cerebral vascular disorder, head trauma, multiple organ failure and extensive burn necessitating intensive treatment); and ulcer caused by a nonsteroidal anti-inflammatory agent. Further, the injectable composition of the present invention is also useful for Helicobacter pylori eradication; suppression of the above-mentioned upper gastrointestinal hemorrhage; treatment and prevention of hyperacidity and ulcer due to postoperative stress; pre-anesthetic administration etc. The injectable composition of the present invention can be administered non-orally (e.g., drip administration, intravenous administration, intramuscular administration, hypodermic administration) for treating or preventing these diseases.

The compound (I) as an active ingredient in the injectable composition of the present invention may be used in combination with other active ingredients (e.g., 1 to 3 other active ingredients).

The "other active ingredients" include, for example, substances having anti-*Helicobacter pylori* action, imidazole-series compounds, bismuth salts, quinolone-series compounds, and so forth. Of these substances, preferred are anti-*Helicobacter pylori* active substances, imidazole-series compounds etc. The "anti-*Helicobacter pylori* active substances" include, for example, antibiotic penicillins (e.g., amoxicillin, benzylpenicillin, piperacillin, mecillinam, etc.), antibiotic cefems (e.g., cefixime, cefaclor, etc.), antibiotic macrolides (e.g., antibiotic erythromycins such as erythromycin, clarithromycin etc.), antibiotic tetracyclines (e.g., tetracycline, minocycline, streptomycin, etc.), antibiotic aminoglycosides (e.g., gentamicin, amikacin, etc.), imipenem, and so forth. Of these substances, preferred are antibiotic penicillins, antibiotic macrolides etc. The "imidazole-series compounds" include, for example, metronidazole, miconazole, etc. The "bismuth salts" include, for example, bismuth acetate, bismuth citrate, etc. The "quinolone-series compounds" include, for example, ofloxacin, ciploxacin, etc. In particular, it is preferred for *Helicobacter pylori* eradication that the injectable composition of the present invention is used in combination with antibiotic penicillins (e.g., amoxicillin) and/or antibiotic erythromycins (e.g., clarithromycin).

The dose per day of the injectable composition varies depending on degree of symptom; age, distinction of sex and weight of a subject of administration; time and interval of administration; species of active ingredients, etc., and is not particularly limited. Its dose per day is about 0.1 to 2 mg/kg weight, and preferably about 0.2 to 1 mg/kg weight, based on the active ingredient (the compound (I)), for example, when non-orally administered as a digestive antiulcer agent to an adult human (60 kg). The injectable composition of the present invention is administered once a day or in 2 to 3 divided portions per day. The concentration of the compound (I) in the injectable composition to be administered is about 0.001 to 40 mg/mL, preferably about 0.01 to 30 mg/mL, and particularly preferably about 0.03 to 10 mg/mL.

INDUSTRIAL APPLICABILITY

According to the injectable composition of the present invention, the solubility of the compound (I) does not decline, and there is no need to employ such a nonaqueous solvent as has a possibility of showing a toxicity when used in high concentration (e.g., polyethylene glycol). Therefore, there is no need to attach a dissolving solution containing a nonaqueous solvent to the injectable composition, and the injectable composition is capable of being dissolved in or diluted with various infusion solutions upon being used at a hospital. Moreover, the injectable composition of the present invention has an excellent stability.

Further, according to a production process of the injectable composition of the present invention, the injectable composition can be produced with a minimum amount of sodium hydroxide to be required, and such injectable composition that a pain or dolor and a local irritation can be relieved can be obtained. Furthermore, since a freeze-dried preparation can be simply produced, decline of pH due to contact with carbon dioxide in an air is not caused, and the high-quality injectable composition can be obtained.

Moreover, according to the present invention, the decline of pH upon producing the injectable composition or redissolving the injectable composition for using can be prevented, and the quality of the injectable composition can be prevented from being deteriorated.

EXAMPLES

The following examples are intended to describe this invention in further detail and should by no means be interpreted as defining the scope of the invention.

Example 1

2-[[[3-methyl-4-(2,2,2-trifluoroethoxy)-2-pyridinyl]methyl]sulfinyl]-1H-benzimidazole (hereinafter, referred to briefly as compound A) (0.509 g) was quickly dissolved in the equivalent amount (in molar ratio) of a sodium hydroxide aqueous solution (0.2 mol/L, 7.32 mL), and a water for injection was added thereto to adjust the total volume to 33.95 mL. The resultant solutions (1 mL and 2 mL) were filled into vials to prepare injectable compositions of formulations 1 and 2 in Table 1. Each preparation is transparent and colorless.

TABLE 1

|  | Formulation 1 | Formulation 2 |
|---|---|---|
| Compound A | 15 mg | 30 mg |
| 0.2 mol/L sodium hydroxide | 0.216 mL | 0.431 mL |
| Water for injection | total 1 mL | total 2 mL |

Example 2

In accordance with the formulation of preparation solution in Table 2, the compound A was dissolved in the equivalent amount (in molar ratio) of a sodium hydroxide aqueous solution (0.2 mol/L), and then mannitol, N-methylglucamine and a water for injection were added thereto to dissolve followed by sterile filtration with a filter (0.22 μm) made from Durapola (manufactured by Nihon Millipore Ltd.) to prepare a preparation solution for injectable composition A.

The resultant preparation solutions for injectable composition A (1 mL and 2 mL) were filled into 5P vial and 9P vial, respectively, to produce aqueous injectable compositions of formulations 1 and 2 in Table 3.

The compound A could be quickly dissolved in the equivalent amount (in molar ratio) of a sodium hydroxide aqueous solution (0.2 mol/L), and the resultant solution was transparent and colorless.

TABLE 2

|  | Formulation of preparation solution |
|---|---|
| Compound A | 9.0 g |
| Mannitol | 18.0 g |
| N-methylglucamine | 3.0 g |
| 0.2 mol/L sodium hydroxide aqueous solution | 129.4 mL |
| Compound A:Sodium hydroxide (molar ratio) | 1:1.06 |
| Water for injection | total 600 mL |

TABLE 3

|  | Formulation 1 | Formulation 2 |
|---|---|---|
| Compound A | 15 mg | 30 mg |
| N-methylglucamine | 5 mg | 10 mg |
| Mannitol | 30 mg | 60 mg |
| 0.2 mol/L sodium hydroxide | 0.216 mL | 0.431 mL |
| Water for injection | total 1 mL | total 2 mL |

Example 3

The preparation solutions for injectable composition A obtained in Example 2 (1 mL and 2 mL) were filled into 5P vial and 17P vial, respectively, and frozen to −40° C. followed by lyophilization by elevating shelf temperatures to 0° C. and 30° C. with keeping a degree of vacuum in a drying oven at 13.3 Pa to produce freeze-dried injectable compositions of formulations 3 and 4 in Table 4.

TABLE 4

|  | Formulation 3 | Formulation 4 |
| --- | --- | --- |
| Compound A | 15 mg | 30 mg |
| N-methylglucamine | 5 mg | 10 mg |
| Mannitol | 30 mg | 60 mg |
| Sodium hydroxide | 1.73 mg | 3.45 mg |

Experimental Example 1

In accordance with the formulations 1 and 2 in Table 5, the compound A was dissolved in 0.2 mol/L sodium hydroxide aqueous solution, and then mannitol, N-methylglucamine and a water for injection were added thereto to dissolve followed by sterile filtration with a filter (0.22 µm) made from Durapola (manufactured by Nihon Millipore Ltd.). The resultant preparation solutions (1 mL and 2 mL) were filled into 9P vial and 17P vial, respectively, followed by lyophilization by the method similar to that of Example 3 to produce freeze-dried injectable compositions of formulations 1 and 2. The qualities of the resultant freeze-dried injectable compositions of formulations 1 and 2 are shown in Table 6.

As apparent from Table 6, the qualities of the injectable compositions are sufficient not only in the case where the freeze-dried injectable composition of the formulation 1 is redissolved in a physiological saline (2.5 mL) but also in the case where the freeze-dried injectable composition of the formulation 2 is redissolved in a physiological saline (5 mL).

TABLE 5

|  | Formulation 1 | Formulation 2 |
| --- | --- | --- |
| Compound A | 15 mg | 30 mg |
| N-methylglucamine | 5 mg | 10 mg |
| Mannitol | 30 mg | 60 mg |
| 0.2 mol/L Sodium hydroxide | 0.216 mL | 0.431 mL |
| Compound A:Sodium hydroxide (molar ratio) | 1:1.06 | 1:1.06 |
| Water for injection | total 1 mL | total 2 mL |

TABLE 6

| Items | Qualities of injectable composition immediately after production |
| --- | --- |
| Formulation 1 | |
| Color of freeze-dried preparation | White |
| Dissolution state of preparation after being dissolved in physiological saline (2.5 mL) | Transparent and colorless |
| Foreign insoluble matter in preparation after being dissolved in physiological saline (2.5 mL) | Free of foreign insoluble matter |
| Particulate matter in preparation after being dissolved in physiological saline (2.5 mL) | Adapted to Japanese Pharmacopoeia 12 |
| Content of Compound A | 14.8 mg |
| Formulation 2 | |
| Color of freeze-dried preparation | White |
| Dissolution state of preparation after being dissolved in physiological saline (5 mL) | Transparent and colorless |
| Foreign insoluble matter in preparation after being dissolved in physiological saline (5 mL) | Free of foreign insoluble matter |
| Particulate matter in preparation after being dissolved in physiological saline (5 mL) | Adapted to Japanese Pharmacopoeia 12 |
| Content of Compound A | 30.0 mg |

Experimental Example 2

In accordance with the formulation 2 in Table 5, the compound A was quickly dissolved in 0.2 mol/L sodium hydroxide aqueous solution, and then mannitol, N-methylglucamine and a water for injection were added thereto to dissolve followed by sterile filtration with a filter (0.22 µm) made from Durapola (manufactured by Nihon Millipore Ltd.). The resultant preparation solution (2 mL) was filled into 17P vial and frozen to −40° C. followed by lyophilization by elevating shelf temperature to 30° C. with keeping a degree of vacuum in a drying oven at 13.3 Pa to produce freeze-dried injectable composition.

The stability of the resultant freeze-dried injectable composition was evaluated by standing the injectable composition at 40° C. and 75% RH. The results are shown in Table 7.

As apparent from Table 7, the freeze-dried injectable composition of the formulation 2 in Table 5 is stable at 40° C. and 70% RH for 6 months, and the qualities of the injectable composition are sufficient. Moreover, it is apparent that the freeze-dried injectable composition of the formulation 1 in Table 5 produced by being filled with a half-volume portion into vials is similarly stable.

TABLE 7

| Items | Immediately after production | 40° C., 3 months | 40° C., 4 months | 40° C., 6 months |
| --- | --- | --- | --- | --- |
| Color of freeze-dried injectable composition | White | White | White | White |
| Dissolution state of injectable composition after being dissolved in physiological saline (5 mL) | Transparent and colorless | Transparent and colorless | Transparent and colorless | Transparent and colorless |
| Foreign insoluble matter in injectable composition after being dissolved in physiological saline (5 mL) | None | None | None | None |
| Content of Compound A (residual ratio (%)) | 100.0% | 99.6% | 99.0% | 98.9% |

Experimental Example 3

In the case (1) where the freeze-dried injectable composition of the formulation 2 obtained in Experimental Example 1 was redissolved in a physiological saline (5 mL) followed by being diluted with a physiological saline (100 mL), and in the case (2) where the freeze-dried injectable composition was redissolved in 5% glucose solution (5 mL) followed by being diluted with 5% glucose solution (100 mL), the transitional stability of each injectable composition was evaluated under irradiation of a white-fluorescent light having 1000 lux. The results are shown in Table 8.

As apparent from Table 8, both injectable compositions (1) and (2) in the cases redissolved in a physiological saline and 5% glucose solution and further diluted with a physiological saline and 5% glucose solution, respectively, are stable for 8 hours, and the qualities of the injectable compositions are sufficient.

TABLE 8

|  | Diluted with physiological saline | | | Diluted with 5% glucose solution | | |
| --- | --- | --- | --- | --- | --- | --- |
|  | 0 hour | After 4 hours | After 8 hours | 0 hour | After 4 hours | After 8 hours |
| Dissolution state | Transparent | Transparent | Transparent | Transparent | Transparent | Transparent |
| Color | Colorless | Colorless | Colorless | Colorless | Colorless | Colorless |
| pH | 9.8 | 9.8 | 9.7 | 9.4 | 9.3 | 9.3 |
| Content of Compound A (residual ratio (%)) | 100.0% | 100.1% | 100.1% | 100.0% | 99.9% | 98.5% |

Experimental Example 4

In accordance with the formulation in Table 9, the compound A was dissolved in 0.2 mol/L sodium hydroxide aqueous solution (1.06 mol of sodium hydroxide relative to 1 mol of the compound A), and then mannitol, N-methylglucamine and a water for injection were added thereto to dissolve followed by sterile filtration with a filter (0.22 μm) made from Durapola (manufactured by Nihon Millipore Ltd.). Each of the resultant preparation solutions (2 mL) was filled into a vial followed by lyophilization to produce a freeze-dried injectable composition. The outer appearance of each freeze-dried injectable composition and the state of each freeze-dried injectable composition when redissolved in a physiological saline (5 mL) are shown in Table 10.

As apparent from Table 10, the injectable compositions obtained by adding 30 to 100 mg of mannitol and 10 to 20 mg of N-methylglucamine relative to 30 mg of the compound A are particularly excellent injectable compositions.

TABLE 9

|  | Formulation | | | | | |
| --- | --- | --- | --- | --- | --- | --- |
|  | 1 | 2 | 3 | 4 | 5 | 6 |
| Compound A (mg) | | | | 30 | | |
| 0.2 mol/L sodium hydroxide (mL) | | | | 0.431 | | |
| Mannitol (mg) | 0 | 30 | 60 | 60 | 100 | 100 |
| N-methylglucamine (mg) | 10 | 10 | 10 | 20 | 10 | 20 |
| Water for injection (total; mL) | | | | 2 | | |

TABLE 10

|  | Formulation | | | | | |
| --- | --- | --- | --- | --- | --- | --- |
|  | 1 | 2 | 3 | 4 | 5 | 6 |
| Appearance[*] | Bad | Good | Good | Good | Good | Good |
| Dissolution state | Opaque and colorless | Transparent and colorless | Transparent and colorless | Transparent and colorless | Transparent and colorless | Transparent and colorless |

[*] Appearance: the term "bad" means that the injectable composition was inappropriate for an injectable composition, and the term "good" means that the injectable composition was appropriate for an injectable composition.

Experimental Example 5

N-methylglucamine solutions (100 mL) in concentrations of 0.1% and 1.0% were prepared. The pH of each preparation solution was adjusted to about 11 with the use of 1 mol/L sodium hydroxide. With stirring each preparation solution, to 0.1% N-methylglucamine solution and 1.0% N-methylglucamine solution was added hydrochloric acid (1 moL/L) in increments of 0.1 mL and 0.5 mL, respectively. The pH of each preparation solution was evaluated. The results are shown in FIG. 1.

As apparent from FIG. 1, both 0.1% and 1.0% N-methylglucamine solutions have buffer capacities at least under the pH of about 9 to 11. Further, it is apparent that 1% N-methylglucamine solution has a buffer capacity in a broad range of pH of about 8 to 11.

Experimental Example 6

The freeze-dried injectable composition obtained in Experimental Example 2 was redissolved in 5 mL of a physiological saline and it was confirmed that pH of the resultant solution was about 11. Moreover, 0.1 mol/L sodium hydroxide was added to 5 mL of the same physiological saline as one used for redissolving to adjust pH of the mixture to about 11. With stirring each preparation solution, 0.1 mol/L hydrochloric acid was added thereto dropwise, and the pH of the redissolved solution was evaluated. The results are shown in FIG. 2.

Figure 2:
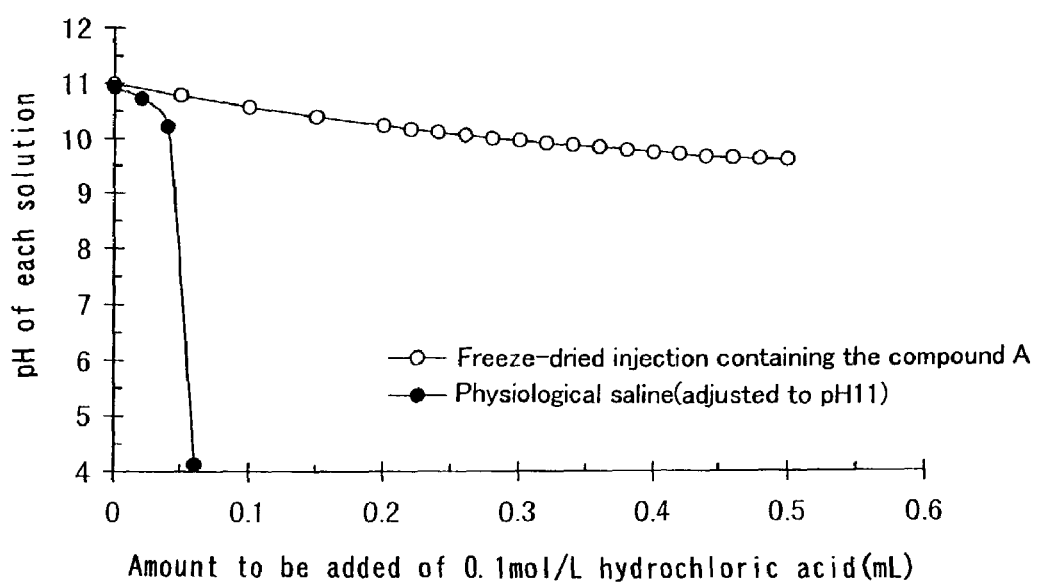
FIG. 2 is the graph demonstrating the results of Experimental Example 6.

As apparent from FIG. 2, the freeze-dried injectable composition containing N-methylglucamine in Experimental Example 2 has a buffer capacity in the range of pH of about 9 to 11. It is apparent that according to the injectable composition of the present invention, the decline of pH can be decreased in the range of pH of about 9 to 11, and the deterioration in quality thereof can be prevented.

The invention claimed is:

1. An injectable composition, comprising:
a compound represented by the formula (I):

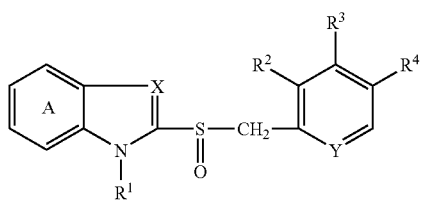

wherein a ring A represents
a benzene ring, or a benzene ring having a substituent selected from the group consisting of
a halogen atom;
a cyano group;
a nitro group;
an alkyl group; or an alkyl group having a substituent selected from the group consisting of a halogen atom; a hydroxyl group; a $C_{1-6}$alkoxy group; a $C_{1-6}$alkoxy-carbonyl group; and a carbamoyl group;
a hydroxyl group;
an alkoxy group; or an alkoxy group having a substituent selected from the group consisting of a halogen atom; a hydroxyl group; a $C_{1-6}$alkoxy group; a $C_{1-6}$alkoxy-carbonyl group; and a carbamoyl group;
an aryl group;
an aryloxy group;
a carboxyl group;
an acyl group;
an acyloxy group; and
a 5- to 10-membered heterocyclic ring,
$R^1$ represents
a hydrogen atom,
an aralkyl group, or an aralkyl group having a substituent selected from the group consisting of a halogen atom; a hydroxyl group; a $C_{1-6}$alkoxy group; a $C_{1-6}$alkoxy-carbonyl group; and a carbamoyl group,
an acyl group, or
an acyloxy group,
$R^2$, $R^3$ and $R^4$ are same or different, each representing
a hydrogen atom,
an alkyl group, or an alkyl group having a substituent selected from the group consisting of a halogen atom; a hydroxyl group; a $C_{1-6}$alkoxy group; a $C_{1-6}$alkoxy-carbonyl group; and a carbamoyl group,
an alkoxy group, or an alkoxy group having a substituent selected from the group consisting of a halogen atom; a hydroxyl group; a $C_{1-6}$alkoxy group; a $C_{1-6}$alkoxy-carbonyl group; and a carbamoyl group, or
an amino group, a mono-$C_{1-6}$alkylamino group, a mono-$C_{6-14}$arylamino group, a di-$C_{1-6}$alkylamino group, or a di-$C_{6-14}$arylamino group,
X represents a nitrogen atom, and
Y represents a nitrogen atom;
N-methylglucamine;
and a strong alkali,
wherein the equivalent ratio of the strong alkali relative to 1 mol of the compound represented by the formula (I) is 0.90 to 1.10
and wherein said composition is dissolvable in or dilutive with a solvent substantially free from a non-aqueous solvent.

2. An injectable composition according to claim 1, wherein, in the formula (I), the ring A represents a benzene ring which may have substituent(s) selected from the group consisting of a halogen atom, a $C_{1-4}$alkyl group which may be halogenated, a $C_{1-4}$alkoxy group which may be halogenated and a 5- or 6-membered heterocyclic group; $R^1$ represents a hydrogen atom; $R^2$ represents a $C_{1-6}$alkyl group, a $C_{1-6}$alkoxy group, a $C_{1-6}$alkoxy-$C_{1-6}$alkoxy group or a di-$C_{1-6}$alkylamino group; $R^3$ represents a hydrogen atom, a $C_{1-6}$alkoxy-$C_{1-6}$alkoxy group, or a $C_{1-6}$alkoxy group which may be halogenated; $R^4$ represents a hydrogen atom or a $C_{1-6}$alkyl group; and X and Y each represent a nitrogen atom.

3. An injectable composition according to claim 1, wherein the compound represented by the formula (I) is a compound represented by the following formula (Ia):

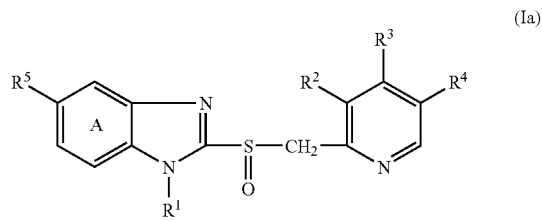

wherein $R^1$ represents a hydrogen atom; $R^2$ represents a $C_{1-3}$alkyl group or a $C_{1-3}$alkoxy group; $R^3$ represents a $C_{1-3}$alkoxy group which may be halogenated or may be substituted with a $C_{1-3}$alkoxy group; $R^4$ represents a hydrogen atom or a $C_{1-3}$alkyl group; and $R^5$ represents a hydrogen atom, a $C_{1-3}$alkoxy group which may be halogenated, or a pyrrolyl group.

4. An injectable composition according to claim 3, wherein, in the formula (Ia), $R^1$ represents a hydrogen atom; $R^2$ represents a $C_{1-3}$alkyl group; $R^3$ represents a $C_{1-3}$alkoxy group which may be halogenated; $R^4$ represents a hydrogen atom; and $R^5$ represents a hydrogen atom or a $C_{1-3}$alkoxy group which may be halogenated.

5. An injectable composition according to claim 1, wherein the strong alkali is an alkali metal compound.

6. An injectable composition according to claim 1, wherein the strong alkali is sodium hydroxide.

7. An injectable composition according to claim 1, the solution of which has a pH of 10.4 to 12.0 in the case where the injectable composition is dissolved with the use of a physiological saline, or a distilled water for injection in a proportion of 2.5 ml relative to 15 mg of the compound represented by the formula (I).

8. An injectable composition according to claim 1, the solution of which has an osmotic pressure ratio of about 0.3 to 5 against a physiological saline in the case where the injectable composition is dissolved with the use of the physiological saline in a proportion of 2.5 ml relative to 15 mg of the compound represented by the formula (I).

9. An injectable composition according to claim 1, which is a freeze-dried preparation.

10. An injectable composition according to claim 1, wherein the amount of N-methylglucamine is about 0.1 to 1 mg relative to 1 mg of the compound represented by the formula (I).

11. An injectable composition according to claim 1, which further comprises a saccharide.

12. An injectable composition according to claim 11, wherein the saccharide is a sugar alcohol.

13. An injectable composition according to claim 11, wherein the saccharide is mannitol.

14. An injectable composition according to claim 11, wherein the amount of the saccharide is about 0.1 to 20 mg relative to 1 mg of the compound represented by the formula (I).

15. An injectable composition according to claim 1, which comprises the compound represented by the formula (I) and is dissolvable in or dilutive with a solvent substantially free from a nonaqueous solvent, and which further comprises about 0.1 to 0.8 mg of N-methylglucamine and about 1 to 10 mg of a sugar alcohol relative to 1 mg of the compound represented by the formula (I).

16. An injectable composition according to claim 1, which comprises the compound represented by the formula (I) and is dissolvable in or dilutive with a solvent substantially free from a nonaqueous solvent, and which further comprises about 4 to 6 mg of N-methylglucamine, about 25 to 35 mg of mannitol and about 1.5 to 1.8 mg of a sodium hydroxide relative to 15 mg of the compound represented by the formula (I).

17. An injectable composition according to claim 1, which comprises 30 mg of the compound represented by the formula (I), 3.45 mg of a sodium hydroxide, 10 mg of N-methylglucamine and 60 mg of mannitol.

18. An injectable composition according to claim 1, which comprises 15 mg of the compound represented by the formula (I), 1.73 mg of a sodium hydroxide, 5 mg of N-methylglucamine and 30 mg of mannitol.

19. A freeze-dried preparation which is dissolvable in at least one liquid selected from (i) water for injection and (ii) infusion solutions, comprises a compound represented by the formula (I) defined in claim 1 and an alkali metal hydroxide in a molar ratio of 1:0.90 to 1.10, and further comprises about 0.1 to 0.8 mg of N-methylglucamine and about 1 to 10 mg of a sugar alcohol relative to 1 mg of the compound represented by the formula (I).

20. A process for preparing an injectable composition which comprises dissolving a compound represented by the formula (I) defined in claim 1 in an aqueous solution of a strong alkali, wherein the concentration of the aqueous solution of the strong alkali is about 0.15 to 0.25 equivalent/L, and the amount of the aqueous solution of the strong alkali is about 1 equivalent relative to 1 mol of the compound represented by the formula (I).

21. A process according to claim 20, wherein the aqueous solution of the strong alkali is an aqueous solution of sodium hydroxide.

22. A method for improving relief of pain and local irritation by an injectable composition, which comprises preparing the injectable composition with the use of a compound represented by the formula (I) defined in claim 1 and a strong alkali in a proportion of about 1 equivalent of the latter relative to 1 mol of the former without a nonaqueous solvent.

23. A method for improving solubility of a freeze-dried preparation in at least one liquid selected from (i) water for injection and (ii) infusion solutions, without using a nonaqueous solvent, which comprises preparing the freeze-dried preparation with the use of a compound represented by the formula (I) defined in claim 1 and a strong alkali in a proportion of about 1 equivalent of the latter relative to 1 mol of the former.

24. A method for treating digestive ulcer, treating ulcers due to postoperative stress, or ulcer caused by a non-steroidal anti-inflammatory agent, which comprises administering a therapeutically effective amount of an injectable composition recited in claim 1 to a human being.

25. A method for treating digestive ulcer or reflux esophagitis, which comprises administering a therapeutically effective amount of an injectable composition recited in claim 1 to a human being.

26. An injectable composition according to claim 1, wherein the compound represented by the formula (I) is 2-[[[3-methyl-4-(2,2,2-trifluoroethoxy)-2-pyridinyl]methyl]sulfinyl]-1H-benzimidazole.

27. A freeze-dried preparation according to claim 19, wherein the compound represented by the formula (I) is 2-[[[3-methyl-4-(2,2,2-trifluoroethoxy)-2-pyridinyl]methyl]sulfinyl]-1H-benzimidazole.

28. A process according to claim 20, wherein the compound represented by the formula (I) is 2-[[[3-methyl-4-(2,2,2-trifluoroethoxy)-2-pyridinyl]methyl]sulfinyl]-1H-benzimidazole.

29. A method according to claim 23, wherein the compound represented by the formula (I) is 2-[[[3-methyl-4-(2,2,2-trifluoroethoxy)-2-pyridinyl]methyl]sulfinyl]-1H-benzimidazole.

* * * * *

UNITED STATES PATENT AND TRADEMARK OFFICE
CERTIFICATE OF CORRECTION

PATENT NO. : 7,396,841 B2
APPLICATION NO. : 10/344805
DATED : July 8, 2008
INVENTOR(S) : Doen et al.

Page 1 of 1

It is certified that error appears in the above-identified patent and that said Letters Patent is hereby corrected as shown below:

Column 5, line 66: "In Particular" should read --In particular--.
Column 8, line 18: "further preferred R" should read --further preferred $R^2$--.
Column 8, line 22: "further preferred R" should read --further preferred $R^3$--.
Column 10, line 17: "awater-soluble" should read --a water-soluble--.
Column 10, lines 22-23: "awater-soluble" should read --a water-soluble--.
Column 12, lines 44: "Dalkyo" should read --Daikyo--.

Signed and Sealed this

Third Day of March, 2009

JOHN DOLL
*Acting Director of the United States Patent and Trademark Office*